United States Patent [19]

Djordjevich et al.

[11] Patent Number: 4,873,987

[45] Date of Patent: Oct. 17, 1989

[54] NONINVASIVE CONTINUOUS MONITOR OF ARTERIAL BLOOD PRESSURE WAVEFORM

[76] Inventors: Ljubomir Djordjevich, 4170 North Marine Dr., Apt. 18H, Chicago, Ill. 60613; Anthony K. Ivankovich, 526 Woodland, Glenview, Ill. 60025

[21] Appl. No.: 213,358

[22] Filed: Jun. 30, 1988

[51] Int. Cl.⁴ .............................................. A61B 5/02
[52] U.S. Cl. ................................... 128/672; 128/681; 128/693
[58] Field of Search ............... 128/672, 677, 680–683, 128/691, 693, 713, 734, 670–671

[56] References Cited

U.S. PATENT DOCUMENTS

3,920,004 11/1975 Nakayama .
3,996,924 12/1976 Wheeler .
3,996,925 12/1976 Djordjevich .
4,144,878 3/1979 Wheeler .
4,437,469 3/1984 Djordjevich ........................ 128/672
4,562,843 1/1986 Djordjevich et al. .............. 128/672
4,718,428 1/1988 Russell ........................... 128/677 X Primary Examiner—Angela D. Sykes
Attorney, Agent, or Firm—Leydig, Voit & Mayer

[57] ABSTRACT

A method, and a device utilizing that method, for continuously, noninvasively measuring a patient's blood pressure. Discrete values of systolic and diastolic blood pressure are noninvasively determined and input to a microprocessor. A continuous non-pressure waveform signal is generated through noninvasive monitoring of the patient and is also input to the microprocessor. The microprocessor calibrates the continuous non-pressure waveform signal using the discrete blood pressure values, thereby generating a continuous waveform signal of blood pressure.

28 Claims, 8 Drawing Sheets

NONINVASIVE CONTINUOUS MONITOR OF ARTERIAL BLOOD PRESSURE WAVEFORM

FIELD OF THE INVENTION

A noninvasive method for continuously determining blood pressure by combining the use of continuous measures of electrical conductance or harmonic analysis and an independent discrete measure of blood pressure through direct physical measurement.

BACKGROUND OF THE INVENTION

It is well known that arterial blood pressure varies quasi-periodically between systolic (highest) and diastolic (lowest) pressure as a consequence of pumping action of the heart. Blood vessels are elastic ducts, made of viscoelastic materials, which expand and contract in unison with the arterial blood pressure. Arterial walls move radially and arterial lumen increases in volume as the heart pumps and decreases in volume between beats. The lumen of the arteries is filled with blood, so that the volume of blood within a section of the body (such as chest or a limb) also varies in unison with the arterial blood pressure.

The expansion and contraction of arterial walls may be detected in many ways: by ultrasound, by x-rays, by electromagnetic imaging, by mechanical devices, by impedance plethysmography and by colorimetry.

Physicians have long sought a safe, noninvasive method for continuous monitoring of arterial blood pressure (ABP) in critical care patients because ABP is the major vital sign indicator. They are currently doing this invasively by sticking probes (needles or catheters) into large arteries. The probes are connected to pressure transducers which transform the detected pressures into images of the waveform, or into a set of numbers indicating the blood pressure variation. The procedure is painful to the patient, cumbersome for medical personnel, and potentially unsafe. It may cause hematoma, damage to the artery, blood clotting and infection.

Any device, capable of providing the same useful service but noninvasively without puncturing, physically penetrating or otherwise harming the patient would be vastly preferable.

There is currently on the market a device called Finapress (manufactured by Ohmeda) which successfully accomplishes the task. A cuff is linked to a control system which contains two essential elements: a color detector and a fast responding pressure-regulating device. The operating principle is to balance the transmural (arterial blood) pressure at all times and restrict the movement of the arterial walls to a minimum. The control loop begins with the very sensitive color detector which detects minute changes of color of the tissues under the cuff, caused by the tendency of the blood to accumulate or decumulate during the blood pressure variation. The detected change provides a command signal to the pressure regulating device to pneumatically adjust the pressure in the cuff, to counteract the transmural arterial pressure variation. This counteracting pressure, which is very similar to the arterial pressure, is then displayed continuously, in real time, as the monitored arterial blood pressure waveform.

The device is complicated and has a very serious limitation: it can operate only on a fingertip, because its mechanics requires a small amount of transparent soft tissue backed by solid bone structure. Unfortunately, the blood flow through the tip of a finger is first to be shut off by the circulating system when a patient approaches shock conditions. Hence, Finapress becomes useless when needed the most. Therefore, a more suitable device, capable of working under all conditions, including shock conditions, would be a substantial improvement in accomplishing the task of reliably, noninvasively and continuously monitoring blood pressure.

U.S. Pat. No. 3,920,004 describes a noninvasive blood pressure sensor utilizing blood flow volume measurements. U.S. Pat. No. 3,996,924 measures venous patency of a human limb by measuring the venous outflow within a defined time interval after release of a forced blockage utilizing electrical impedance measurements. U.S. Pat. Nos. 3,996,925, 4,437,469 and 4,562,843 describe systems for determining characteristics of blood flow; however, there is no description of a device capable of noninvasive continuous blood pressure measurements.

SUMMARY OF THE INVENTION

New techniques and apparatus are described for continuously monitoring arterial blood pressure. The method requires the production of a continuous trace of the pressure wave with high fidelity and the measurement of systolic, diastolic and mean blood pressure. The method is based upon the observation that there is proportionality between the arterial blood pressure and electrical conductance in a section of the human body. The movement of the viscoelastic walls of arteries expanding and contracting as the heart beats results in a change in the volume of blood in the lumen of the arteries. Since the electrical conductivity of the blood volume is 10 to 1,000 times greater than that in other tissues of the body, the conductance measurements are specific for detecting the conductance principally of the blood. Therefore, there is a proportional change in conductance as the volume of blood in the artery changes and this change in conductance is proportional to the increase in blood pressure. During systole there is an increase in electrical conductance because of the increased pressure and, therefore, expansion of the arteries. During diastole, the opposite takes place as the volume decreases and the conductance of the blood decreases.

The method of the present invention comprises the continuous measurement, recording and processing of conductance in a portion of an artery which continues to experience arterial blood pressure under normal and shock conditions. The conductance value may be plotted as a blood pressure waveform (P-wave), the conductance (C-wave) or the electrical resistance (Z-wave). Any noninvasive blood pressure measuring procedure (for example, a pressure cuff) may be used to determine the systolic (PS or $P_S$), diastolic (PD or $P_D$) and the mean (PM or $P_M$) pressure. A microprocessor connected thereto automatically records the values for the systolic, diastolic, mean pressure and heart rate. Electrodes for detecting electrical resistance are attached to the patient's body adjacent the artery. The electrical resistance measurements and the discrete blood pressure measurements are transferred to and recorded by the microprocessor. The direct measurement of the blood pressure values are used to calibrate the electrical conductance signals such as to allow the determination of the blood pressure values in a continuous manner.

The resulting blood pressure waveform obtained in this manner is very similar to that obtained from a transducer inserted into an arterial line.

BRIEF DESCRIPTION OF THE DRAWINGS

FIG. 6b illustrates increasing pressure in a cuff, while FIG. 6a, line K illustrates the undeformed conductance signal below the diastolic pressure; line L illustrates the diastolic pressure (PD); line M illustrates the pattern when the cuff pressure reaches the maximum (PM); and line N illustrates when the cuff pressure becomes so great that the blood flow is first blocked and is a measure of the systolic pressure (PS).

DESCRIPTION OF SPECIFIC EMBODIMENTS

Figure 1:
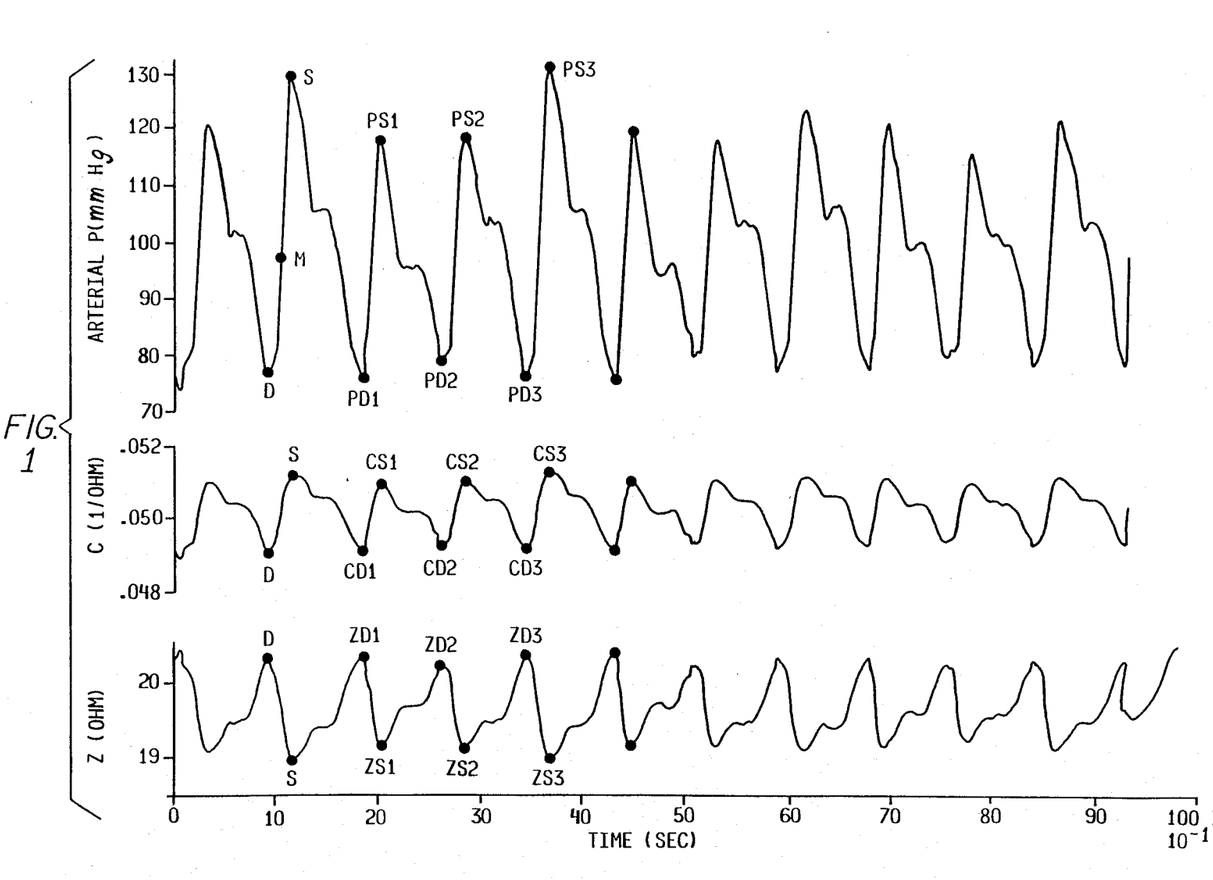
FIG. 1 illustrates the profile of the Z-wave, C-wave and P-wave steps resulting from resistance to the arterial pressure wave-form.

A new technique for continuously monitoring a patient's arterial blood pressure waveform is described and explained herein. The technique is capable of producing a continuous trace of a pressure wave with high fidelity, as well as a measurement of systolic diastolic and mean pressure. The present invention is based upon the principle that there is proportionality between the arterial blood pressure and electrical conductance in a section of the human body. More specifically, the viscoelastic walls of arteries expand and contract in unison with the quasi-periodic variations of blood pressure. This, in turn, results in corresponding accumulations and decumulations of blood in lumen of arteries. Because the electrical conductivity of blood is 10 to 1,000 times greater than that of other tissues in the body, the technique preferentially measures the conductance of the blood. Therefore, the blood accumulation in arteries during systole produces an increase of electrical conductance proportional to the increase of blood pressure. During diastole, the opposite takes place. This is demonstrated in FIG. 1. The blood pressure variation (P-wave) is the top trace, the conductance (C-wave) is the middle trace and the bottom trace is the electrical resistance (Z-wave), which is the inverse of the conductance.

The method of producing the P-wave from the C-wave requires calibration by means of independently measured systolic, diastolic and mean pressure. In one embodiment, the experimental setup consists of an 80283 microprocessor (CPU) interfaced with an analog/digital (A/D) converter to an IFM (model 400) resistance meter and a noninvasive blood pressure measuring device to measure systolic (PS), diastolic (PD) and mean (PM) pressure. One type of device for such a measurement is a pressure cuff placed on the patient's arm.

The placement of electrodes for the detection of conductance (or resistance) on the upper arm or chest enables the blood pressure monitoring device to function under shock conditions. Under shock conditions, peripheral regions, such as fingers, lose a reliable supply of blood. Therefore, such regions are not suitable for the measurement of blood pressure under shock conditions.

The apparatus of the present invention, once calibrated, discloses the P-wave display continuously. However, it may be reset at any time by recalibration whenever there is a possibility of significant change due to vasodilation or constriction. The method of the present invention allows the continuous noninvasive monitoring of arterial blood pressure where other noninvasive monitoring techniques may fail due to a insufficient or intermittent supply of blood, such as under shock conditions.

There are three methods for calibrating the device of the present invention wherein the continuous conductance is utilized to continuously monitor the blood pressure values. These three of calibration utilizes an independent, discrete arterial blood pressure (ABP) measurement such as by a pressure cuff sphygmomanometer, Korotkoff sound detector Dinamap ®, Critikon ® or Datascope ®.

A second method of calibrating utilizes a pressure cuff in combination with the measurement of conductance wherein the changes in conductance reflect the blood pressure values. A third method of calibrating the continuous conductance measurements requires harmonic analysis wherein a spectrum of frequencies is utilized and changes in the power spectrum of the harmonic frequencies indicate the discrete blood pressure values.

The continuous waveform signal may also be determined by ultrasonic monitoring of arterial wall movement, x-ray imaging of arterial wall movement, microwave imaging, nuclear, magnetic resonance (NMR) imaging or colorimetry.

METHOD 1

Continuous Conductance Calibrated by Independent Discrete ABP Measurements

A first embodiment of the present invention is based on continuously monitoring the electrical conductance (C) of a section of the human body, and translating the variation of C into the blood pressure (P) variation, as follows.

Figure 2:
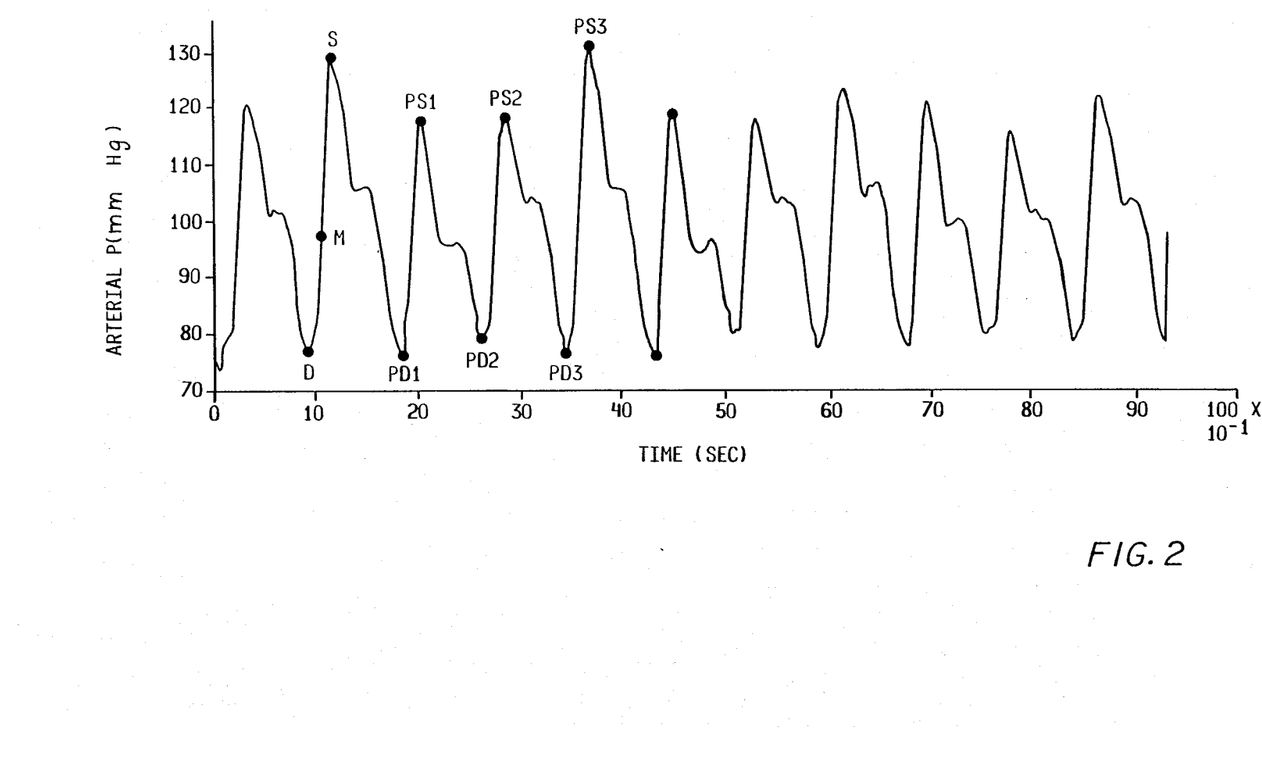
FIG. 2 illustrates the P-wave measuring arterial blood pressure increases from D (diastolic) to S (systolic) for succeeding beats of the heart illustrated by the numbers 1, 2, 3, etc.
Figure 3:
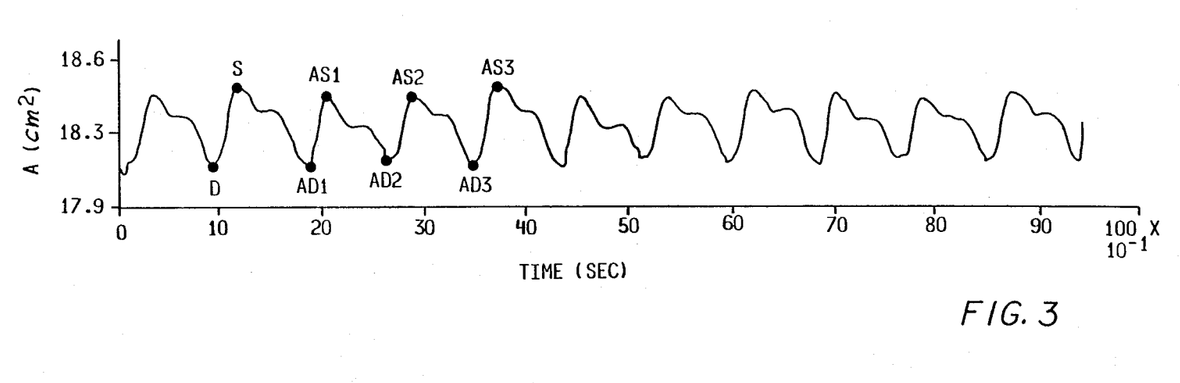
FIG. 3 indicates the cross-sectional area (A) of arteries.

When during systole arterial blood pressure (ABP) increases from a minimum value D to a maximum value S (see FIG. 2), the cross-sectional area (A) of the arteries also increases (see FIG. 3) in proportion to the ABP. According to Ohm's law, $$C = \frac{A}{\rho L}$$

the conductance (C) of a particular material is inversely proportional to the resistivity ($\rho$) of the material and the distance (L) between the measuring electrodes. Every conductor is also a resistor, with the resistance being directly proportional to the length and inversely proportional to the cross-sectional area. Since the length between measuring electrodes is constant, as is the resistivity, the conductance is proportional to the cross-sectional area only, in this case principally that of the blood volume in the artery.

Figure 4:
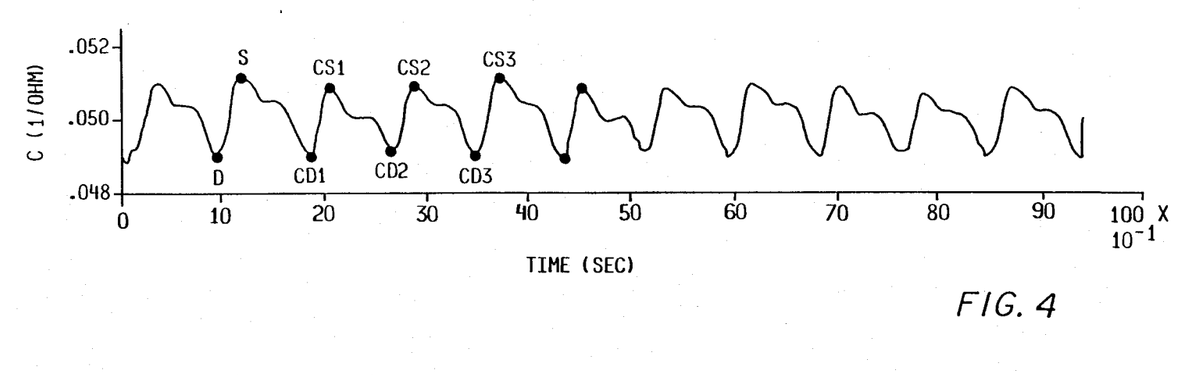
FIG. 4 illustrates the conductance of a section of the body during the cardiac cycle.

Blood plasma is an electrolyte with resistivity 10 to 100 times smaller than the resistivity of soft tissues and 1000 times smaller than the resistivity of bones. Therefore, the conductance of a section of the body changes strongly during the cardiac cycle, as seen in FIG. 4, in direct proportion with the variation of A and P, as illustrated by dramatic similarity of waveforms in FIGS. 2, 3 and 4.

In the device of the present invention, the electrical conductance is continuously monitored using an electrode device (such as an IFM 400) in a limb or the chest of a patient where blood flow continues, even during shock. Therefore, the electrode device continuously produces a waveform as in FIG. 4, and provides that waveform to a microprocessor. The microprocessor uses this information to calculate and store average values of the conductance at systole and diastole (CS and CD, respectively) and, if desired, a mean conductance CM.

To obtain a corresponding pressure waveform, the C-waveform must be calibrated with simultaneously-taken blood pressure mesurements from an independent noninvasive discrete blood pressure measuring device (such as sphigmomanometer, Korotkoff sounds, Dinamap ®, Critikon ®, Datascope ®, etc.). These conventional discrete ABP measuring devices noninvasively measure systolic, diastolic and mean blood pressure (obtained during a series of 10-15 cardiac cycles), but do not produce a continuous waveform. The values of the systolic, diastolic and mean ABP (PS, PD and PM) measured by the discrete device are stored in the microprocessor, where they are assigned to the average values CS and CM, (see FIG. 4) of the conductance curve. Thus, the discrete measurements are used to calibrate the continuous electrical conductance measurements. This three-point calibrating procedure establishes the proportionality between the ABP and the C-waveform. Three-point calibration results in a quadratic mapping of the C-waveform into the P-waveform, which produces a non-linear, high fidelity correlation. If only two points, say systolic PS and diastolic PD pressures, are used to calibrate the C-waveform with ABP, the calibration is linear and the resulting P-waveform is linearly similar to the C-waveform.

Once the correlation (calibration) between the C-waveform and systolic, diastolic and mean ABP is established, monitoring of the P-waveform proceeds indefinitely by monitoring only the C-waveform using the electrode device. The continuous conductance measurements are provided to the microprocessor, which interpolates the stored conductance data (CS, CD and CM) and the corresponding ABP data (PS, PD and PM) to generate a continuous P-waveform. This Method 1 is illustrated in Examples 1 and 2.

METHOD 2

Continuous Conductance and Pressure Cuff

Method 2 differs from Method 1 in that it does not require an independent discrete ABP measuring device to obtain PS, PD and PM for calibration purposes. Rather, the device determines those pressure values by itself.

The preferred technique is again to continuously monitor the electrical conductance (or impedance) in a section of the patient's limb. Here, the measuring electrodes (either bipolar or tetrapolar) are attached either to the wall of the pressure cuff interfacing the skin of the patient, or distally from the cuff on the same limb. The electrodes are connected to the air pump or a pressurized air reservoir.

Figure 5A:
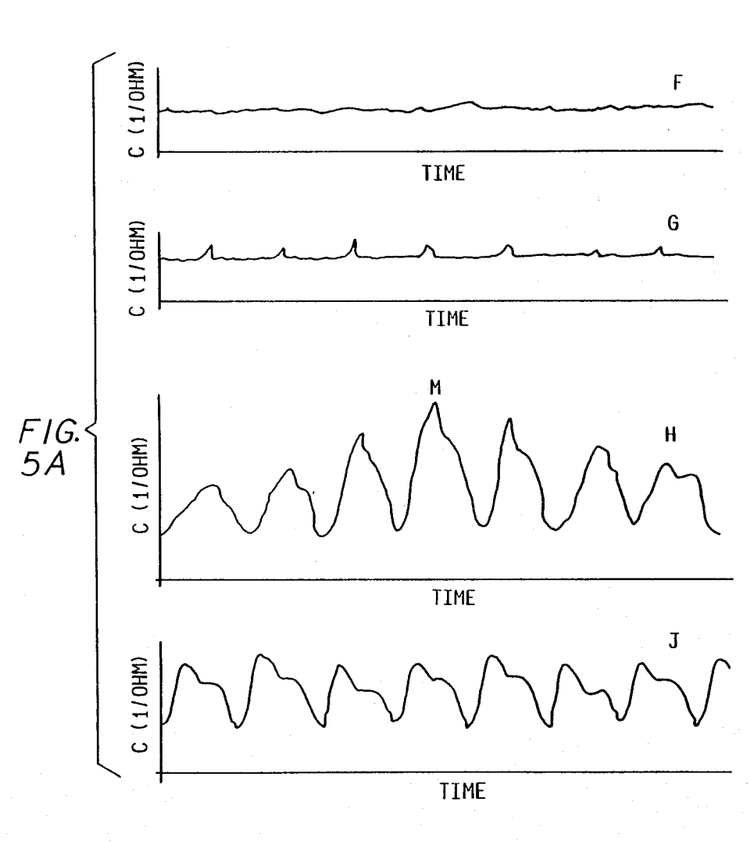
FIG. 5a illustrates the conductance (or impedance) as a function of reduced pressure in a cuff (shown in FIG. 5b) wherein line F illustrates the cuff in a fully inflated position; line G illustrates when the pressure of the cuff equals the systolic arterial pressure; line H illustrates when the cuff pressure becomes less and the amplitude C becomes maximum; and line J illustrates the diastolic pressure (PD).

At the beginning of the monitoring, the cuff is inflated and the pressure raised until the conductance (or impedance) signal becomes flat as in FIG. 5a, line F). Subsequently, the cuff is deflated so that the pressure in the cuff decreases steadily at a slow rate. When the pressure in the cuff equals the systolic arterial pressure, tiny blips on the conductance (or impedance) signal trace appears as in FIG. 5a, line G. When the first such blip occurs, the corresponding cuff pressure is tagged and stored in the microprocessor's memory as systolic blood pressure (PS). As the cuff pressure decreases, the amplitudes of the C (or Z) signal become bigger and bigger, as in FIG. 5a, line H. When the amplitude of the signal becomes maximum (like M on line H), the corresponding cuff pressure is tagged as the mean arterial pressure (PM) and stored in the memory of the microprocessor. As the cuff pressure decreases even further, at one point the peak of the C waves (or bottom of the Z wave) will appear as fully developed, as in line J in FIG. 5a. The cuff pressure at which this occurs is tagged as diastolic pressure (PD) and stored in the memory. The cuff is then completely deflated.

All three pressures (PS, PM, PD) are used in the microprocessor for the calibration of fully developed conductance (or impedance) waves, as in Method 1.

Figure 6A:
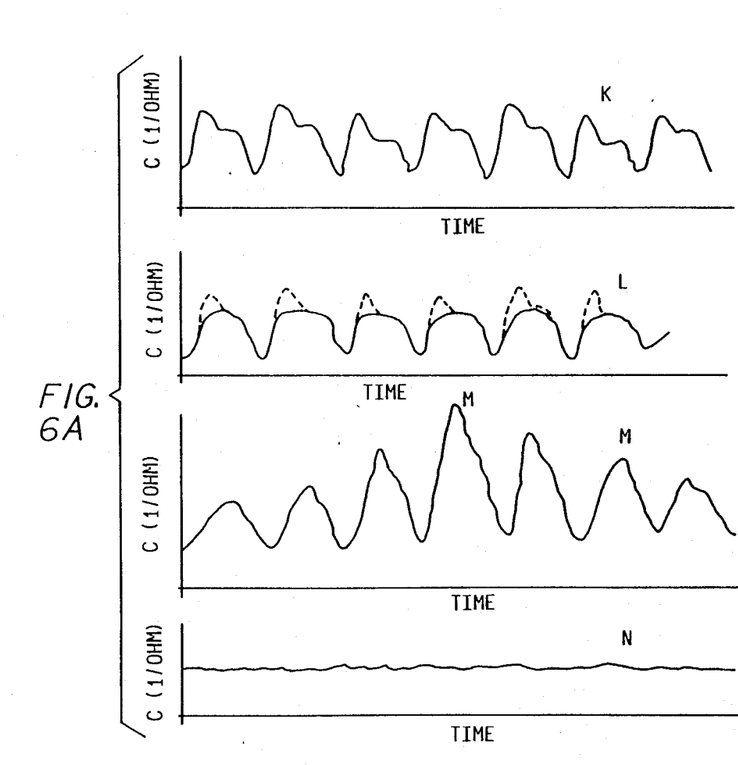
Figure 6B:
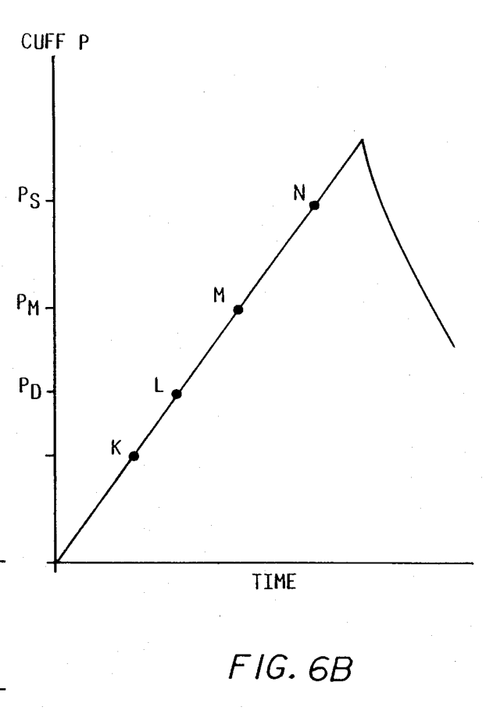

The pressure determination process may also be reversed. Thus, the cuff is slowly inflated, as in FIG. 6b. In the beginning, the conductance signal is undeformed, fully developed, as long as the cuff pressure is below the diastolic pressure, as in line K in FIG. 6a. When cuff pressure reaches PD, the peaks of the conductance curve start flattening as in FIG. 6a, line L (or the bottoms of the impedance curve will flatten). The cuff pressure at which this flattening is first detected is marked PD. When the cuff pressure reaches PM, the amplitudes of the waveform becomes maximum, as in line M. When the waves disappear (line becomes flat), the pressure is PS. Hence, this embodiment is capable of determining the systolic, diastolic and mean arterial pressure in a new manner as a discrete noninvasive device, which can operate as such (without the continuous monitoring mode). However, the PS, PD and PM can also be used to calibrate the conductance waveform, as in Method 1, and thus produce a continuous noninvasive P-waveform. Hence, this embodiment may be used for both discrete and continuous measuring of the arterial blood pressure.

METHOD 3

Continuous Conductance and Calibration Utilizing Harmonic Analysis

It is a well known fact that when elastic materials are exposed to tension, they tend to vibrate with frequencies proportional to the magnitude of the stress. For example, the higher tension in a violin string produces a tone of higher pitch.

This principle is used in Method 3 to determine the occurrence of systolic, diastolic and mean arterial pressure.

The preferred technique to use here is known as harmonic analysis. This analysis decomposes the waveform into a set of sine and cosine waves (spectrum) with frequencies which are integer multiples of the basic frequency $f_1$, which is, in this case, the reciprocal of the duration of the cardiac cycle T.

$$f_1 = \frac{1}{T} [\text{sec}^{-1}]$$

The first higher frequency ("first harmonic") is $f_2 = 2f_1$, then $f_3 = 3f_1, \ldots f_4 = 4f_1, \ldots$, etc.

The $n^{th}$ component will have the form:

$$C_n = A_n \text{COS}(nf_1 + X_n) + B_n \text{SIN}(nf_1 + Y_n)$$

where $A_n$ and $B_n$ are amplitudes and $X_n$ and $Y_n$ are the phase differences.

Figure 7:
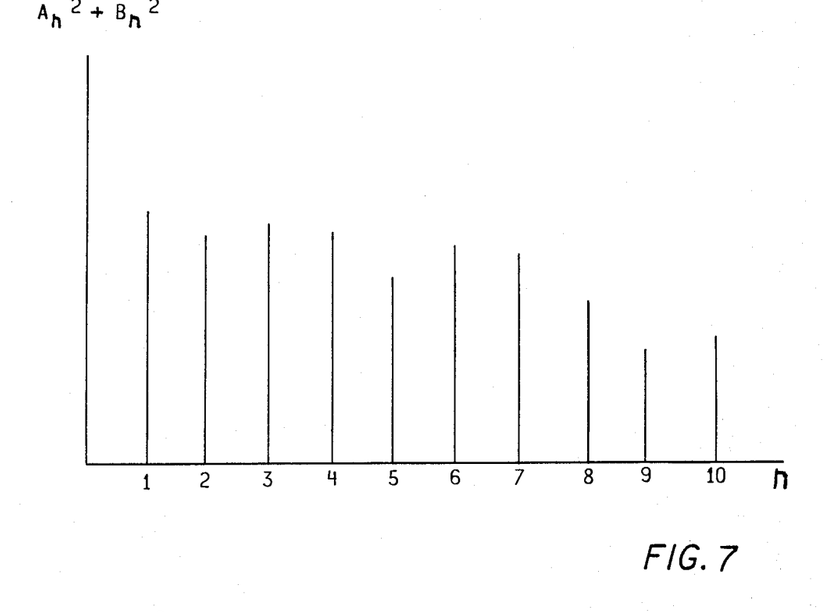
FIG. 7 is the power spectrum at high pressure when the artery becomes richer in high frequency components.
Figure 8:
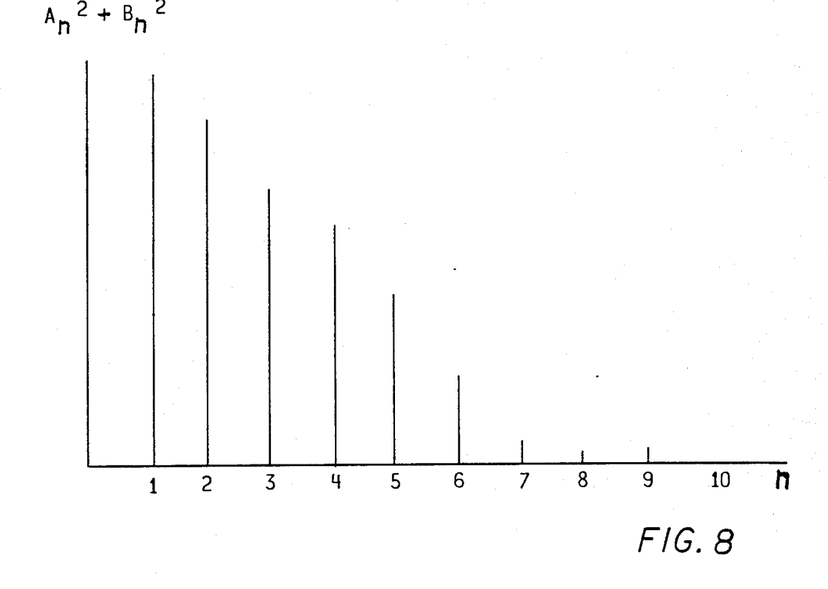
FIG. 8 illustrates the power spectrum at low pressure wherein the larger amplitudes are at lower frequencies.

As the blood pressure increases in the artery, the spectrum becomes richer in the high frequency components. The set of squares of all amplitudes ($A_n^2$, $B_n^2$) is known as the power spectrum. Thus, the power spectrum at high pressure (FIG. 7) has larger amplitudes of high frequency components (n is large), than the power spectrum at low pressure (see FIG. 8).

Figure 5B:
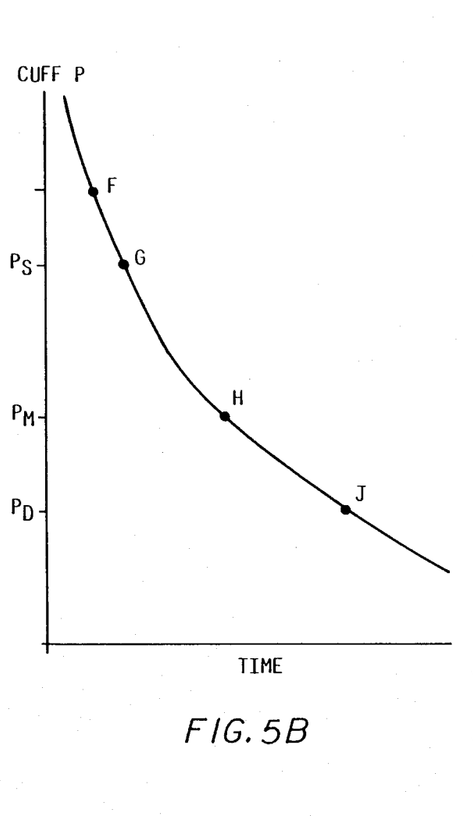
Figure 9:
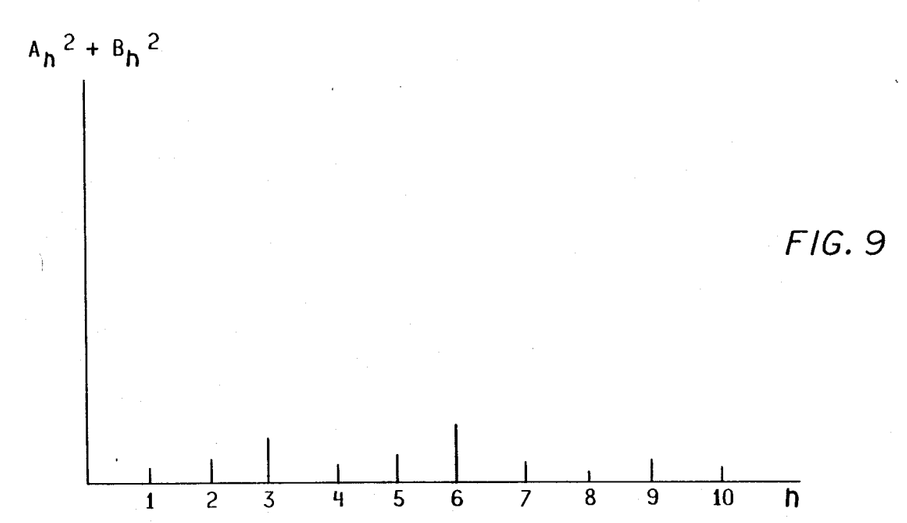
FIG. 9 illustrates the power spectrum for the plain noise background.

This pattern is used to determine systolic, diastolic and mean arterial pressure. The system again consists of the electrical conductance (or impedance) monitor and an inflatable cuff. In the beginning of measurement the cuff pressure is rapidly raised until the conductance (impedance) trace becomes essentially flat, as line F in FIG. 5a. As the cuff pressure decreases the pattern of the waveform changes progressively to FIG. 5a, lines G, H and J, as in the Method 2. In this method, however, the waveform is continuously analyzed by the microprocessor by fast Fourier transform (FFT) analysis to continuously determine the power spectrum of the signal. When the cuff pressure equals PS, the spectrum suddenly changes from the one resembling FIG. 9 (plain noise) to the one resembling FIG. 7. When the microprocessor detects this change, it tags the corresponding cuff pressure as PS. As the cuff pressure decreases, as in FIG. 5b, the power spectrum will progressively resemble FIG. 8 more than FIG. 7. When the change of the pattern of the power spectrum essentially stops, the corresponding cuff pressure is tagged as PD. Hence, the device is used to determine the systolic and the diastolic pressure as a discrete noninvasive device.

To achieve a continuous monitoring mode, PS and PD as determined above are used in the microprocessor to calibrate the conductance waveform, similar to Method 1. The mean pressure of the individual cardiac cycle, PM, is obtained by integrating (in the microprocessor) the calibrated P-wave signal P(t) and dividing with the duration of the cardiac cycle, i.e., $$PM = \frac{1}{T} \int_{1 \text{ cycle}} P(t) dt$$

The mean pressure over several cardiac cycles is obtained by integrating over long period of time, T:

$$PM = \frac{1}{T} \int_{\text{many cycles}} P(t) dt$$

EXAMPLE 1

Continuous Conductor and Independent Discrete ABP Measurements

Figure 10:
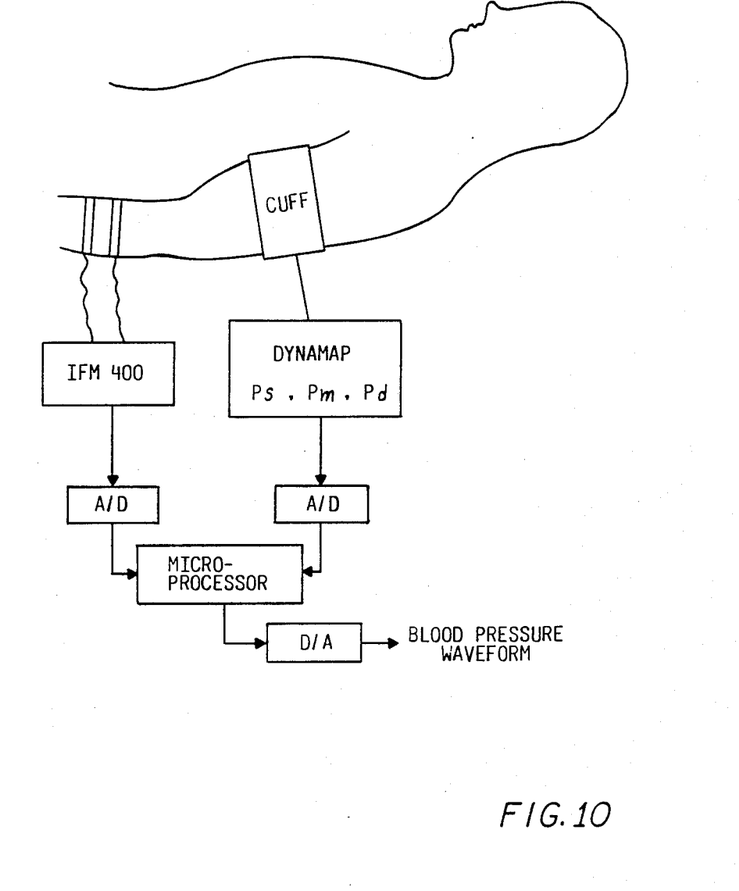
FIG. 10 illustrates the arm of the patient with a measuring cuff and strip electrodes in place. The IMF 400 is a mod-400 IFM electrical impedance meter; the cuff is attached to a Dinamap ® for determining blood pressure parameters (PS, PM, PD).
Figure 11:
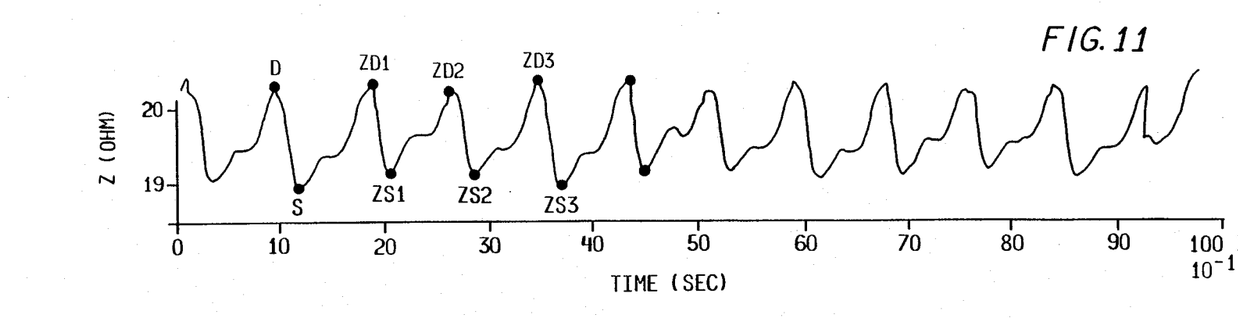
FIG. 11 illustrates the Z-wave illustrating the variation of electrical impedance of the section of the forearm between two electrodes.

ABP measuring cuff is placed on the left upper arm of the patient as in FIG. 10. The cuff is linked to a Dinamap ®. Four strip electrodes are placed on the right forearm. The electrodes are linked to a Mod 400 IFM electrical impedance meter. The meter produces a 100 Khz alternating electric field between the two outer electrodes. Two inner electrodes are the measuring electrodes. All four electrodes are part of a tetrapolar impedance meter bridge system which continuously measures the variation of electrical impedance of the section of the forearm between the two inner electrodes. The output of the meter is an analog signal (voltage), as represented in FIG. 11, which is proportional to the impedance Z (ohms). The analog signal is fed into a microprocessor (digital DEC 11/03) via an analog/digital converter with sampling rate of 100/second. The microprocessor first calculates conductance from each sampled impedance Z by the simple formula:

$$C = \frac{1}{Z}$$

It simultaneously calculates the sliding averages of CS and CD and the mean value (CM) of the C-waveform, as the function of time. The Dinamap ® measures at the beginning of measurement the systolic (PS), diastolic (PD) and the mean (PM) arterial pressure. As soon as the results are available, they are automatically transferred to the microprocessor, which calculates the calibration factors by correlating PS with CS, PD with CD and PM with CM. The factors are then used to multiply every point in the C-waveform (FIG. 4) to obtain the P-waveform (FIG. 2), which is displayed via digital/analog conversion on the screen of the CRT as a real-time signal representing the P-waveform. The CRT also displays the numerical values (in mmHg) of PS, PD and PM.

A pressure cuff is placed on a patient's arm and the inflation and deflation is automatically controlled by the microprocessor. The values of the systolic, diastolic, mean pressure and heart rate are automatically transferred to the CPU. The signal-processing steps are as follows:

The converted Z-wave is first transformed into a C-wave. The sliding average of the numerical values of the peaks (CS) and modums (CD) of the C-wave is continuously calculated. In addition, a sliding mean value (CM) of the C-wave is also calculated. The signal is calibrated by assigning a value of PS to that value of CS which is obtained during the time of measuring PS. Similarly, PD is assigned to CD and PM to CM. The numerical values of pressures corresponding to other points on the C-wave are calculated from this three-point calibration. The signal, transformed by the calibration algorithm is displayed on a cathode ray tube screen as a continuous P-wave signal.

The fluctuation of the sliding PM value is used as an indicator for renewing the calibration of the waves. When PM shows a significant deviation (10% or more) from the assigned value, sustained for more than 20 seconds, the CPU starts a recalibration process which then assigns new PS, PM and PD values to CS, CM and CD. The minimum, but sufficient, sampling rate for high-fidelity P-wave is 100 times per second.

The result of the processing of the conductance signal is a waveform very similar to the blood pressure waveform obtained from a transducer attached to an arterial line. In the present case, the average PS is 128 torr, the average PM is 98 torr and the PD is 82 torr.

The average value is calculated over cardiac cycles occurring during 20 second intervals. These values are the same as the values obtained from the Dinamap ®, as expected, since these values are forced by assigning. The accuracy of the blood pressure measurement was the same as that of the calibrating instrument, that is within 5-10% of the true values.

EXAMPLE 2

Method of Example 1 Utilizing

EKG Type Electrodes

The setup is the same as in Example 1, except that two button (EKG) type electrodes are placed on the patient, one immediately underneath the left clavicle and the other at the tip of the sternum. In this bipolar arrangement, each electrode serves both as a field-producing and as a measuring electrode. The rest of the system and the operation is the same as in Example 1.

We claim:

1. A method of continuously, noninvasively measuring blood pressure, said method comprising the steps of:
    noninvasively determining at least discrete systolic and diastolic blood pressure values;
    simultaneously, noninvasively monitoring the patient with a waveform signal means to generate a sample continuous non-pressure waveform signal;
    inputting said discrete systolic and diastolic blood pressure values and said sample continuous non-pressure waveform signal to a microprocessor;
    calculating at least systolic and diastolic points for said sample continuous non-pressure waveform signal;
    calibrating said systolic and diastolic points with said systolic and diastolic blood pressure values, respectively, and storing said calibrated information;
    continuously, noninvasively monitoring said patient with said waveform signal means to generate a continuous non-pressure waveform signal;
    using said calibrated information to transform said continuous non-pressure waveform signal into a continuous blood pressure waveform.

2. The method of claim 1 wherein said noninvasive discrete determination of at least systolic and diastolic blood pressure values is made using one of the following: a pressure cuff, sphygmomanometer, or Korotkoff sound detector.

3. The method of claim 1 wherein said waveform signal means measures electrical conductance and generates a conductance waveform signal.

4. The method of claim 3 where in said noninvasive discrete determination of at least systolic and diastolic blood pressure values is made by analyzing the power spectrum of the conductance signal.

5. The method of claim 4 wherein the power spectrum is analyzed using a fast Fourier transform technique.

6. The method of claim 4 wherein the waveform signal generated is selected from the following: Z-wave or C-wave.

7. The method of claim 3 wherein said noninvasive discrete determination of at least systolic and diastolic blood pressure values is made by gradually deflating a pressure cuff and simultaneously detecting changes in the conductance waveform signal.

8. The method of claim 1 further comprising the step of determining the pulse rate by counting waves in said continuous non-pressure waveform signal.

9. The method of claim 1 wherein said waveform signal means measures electrical impedance.

10. The method of claim 1 wherein said waveform signal means ultrasonically monitors arterial wall movement.

11. The method of claim 1 wherein said waveform signal means performs X-ray imaging of arterial wall movement.

12. The method of claim 1 wherein said waveform signal means performs microwave imaging.

13. The method of claim 1 wherein said waveform signal means performs NMR imaging.

14. The method of claim 1 wherein said waveform signal means makes colorimetric measurements.

15. A device for continuously, noninvasively measuring blood pressure, said device comprising:
    a pressure signal means for noninvasively determining at least discrete systolic and diastolic blood pressure values for a patient;
    a waveform signal means for noninvasively monitoring said patient to generate a continuous non-pressure waveform signal; and
    microprocessing means for receiving at least said discrete systolic and diastolic blood pressure values and said continuous non-pressure waveform signal as inputs, said continuous non-pressure waveform signal being calibrated using at least said discrete systolic and diastolic blood pressure values to generate a continuous waveform signal of blood pressure.

16. The device of claim 15 wherein said pressure signal means is one of the following: a pressure cuff, sphygmomanometer, or Korotkoff sound detector.

17. The device of claim 15 wherein said waveform signal means measures electrical conductance and generates a conductance waveform signal.

18. The device of claim 17 wherein said conductance waveform signal comprises one of the following: C-wave or Z-wave.

19. The device of claim 17 wherein said pressure signal means comprises at least a portion of the microprocessing means which analyzes the power spectrum of the conductance waveform signal.

20. The device of claim 9 wherein the microprocessing means analyzes the power spectrum is using a fast Fourier transform technique.

21. The device of claim 17 wherein said pressure signal means comprises a pressure cuff and at least a portion of the microprocessing means which detects changes in the conductance waveform signal as the pressure cuff is gradually deflated.

22. The device of claim 15 wherein said waveform signal means measures electrical impedance.

23. The device of claim 15 wherein said waveform signal means ultrasonically monitors arterial wall movement.

24. The device of claim 15 wherein said waveform signal means performs X-ray imaging of arterial wall movement.

25. The device of claim 15 wherein said waveform signal means performs microwave imaging.

26. The device of claim 15 wherein said waveform signal means performs NMR imaging.

27. The device of claim 15 wherein said waveform signal means makes colorimetric measurements.

28. The device of claim 15 further including means for determining pulse rate by counting waves in said continuous non-pressure waveform signal.

* * * * *

UNITED STATES PATENT AND TRADEMARK OFFICE
CERTIFICATE OF CORRECTION

PATENT NO. : 4,873,987　　　　　　　　　　　　Page 1 of 2
DATED      : October 17, 1989
INVENTOR(S): Ljubomir Djordjevich and Anthony K. Ivankovich It is certified that error appears in the above-identified patent and that said Letters Patent is hereby corrected as shown below:

Col. 4, line 40, cancel "These three" and insert --A first method--;

line 42, after "cuff", insert a comma (,);

line 43, after "detector", insert a comma (,);

line 57, after "nuclear", delete the comma (,).

Col. 8, line 5, correct the formula as follows:

$$PM = \frac{1}{T} \int_{1 \text{ cycle}} P(t)dt$$

line 11, correct the formula as follows:

$$PM = \frac{1}{T} \int_{\text{many cycles}} P(t)dt$$

UNITED STATES PATENT AND TRADEMARK OFFICE
CERTIFICATE OF CORRECTION

PATENT NO. : 4,873,987

DATED : October 17, 1989

INVENTOR(S) : Ljubomir Djordjevich, et al

It is certified that error appears in the above-identified patent and that said Letters Patent is hereby corrected as shown below:

Col. 10, line 11, cancel "claim 4" and insert --claim 3--;

line 66, cancel "claim 9" and insert --claim 19--;

line 67, cancel "is".

Signed and Sealed this

Twenty-fifth Day of September, 1990

Attest:

HARRY F. MANBECK, JR.

*Attesting Officer*   *Commissioner of Patents and Trademarks*